United States Patent [19]
Nishioka et al.

[11] Patent Number: 4,721,359
[45] Date of Patent: Jan. 26, 1988

[54] ILLUMINATING OPTICAL SYSTEM FOR ENDOSCOPES

[75] Inventors: Kimihiko Nishioka; Susumu Takahashi, both of Hachiouji, Japan

[73] Assignee: Olympus Optical Co., Ltd., Tokyo, Japan

[21] Appl. No.: 741,581

[22] Filed: Jun. 5, 1985

[30] Foreign Application Priority Data

Jun. 8, 1984 [JP] Japan ............................ 59-117931

[51] Int. Cl.[4] ............................................. G02B 23/26
[52] U.S. Cl. ............................. 350/96.26; 350/96.18
[58] Field of Search ............... 350/96.18, 96.26, 168, 350/453, 481, 523

[56] References Cited

U.S. PATENT DOCUMENTS

| | | | |
|---|---|---|---|
| 4,294,511 | 10/1981 | Yamashita et al. | 350/96.18 |
| 4,390,012 | 6/1983 | Mizumoto | 350/96.26 |
| 4,427,977 | 1/1984 | Carollo et al. | 350/96.18 |
| 4,483,585 | 11/1984 | Takami | 350/96.26 |
| 4,576,435 | 3/1986 | Nishioka | 350/96.26 |
| 4,588,265 | 5/1986 | Takahashi | 350/453 |

FOREIGN PATENT DOCUMENTS 55-11216  1/1980  Japan .

*Primary Examiner*—William L. Sikes
*Assistant Examiner*—Robert E. Wise
*Attorney, Agent, or Firm*—Cushman, Darby & Cushman

[57] ABSTRACT

In order to make it possible to uniformly illuminate the surface of an object to be observed, an illuminating optical system for endoscopes comprises a light supplying side light guide, a light receiving side light guide arranged as spaced from and aligned with the light supplying side light guide and a connecting optical system arranged between the light supplying side light guide and light receiving side light guide and consisting of at least one convex lens and one concave lens. A concave lens for expanding the light bundle is arranged in front of the exit end of the light receiving side light guide. A light intercepting member intercepting a part of the light bundle in response to the brightness distribution on the object image surface may be provided between the light supplying side light guide and light receiving side light guide.

8 Claims, 9 Drawing Figures

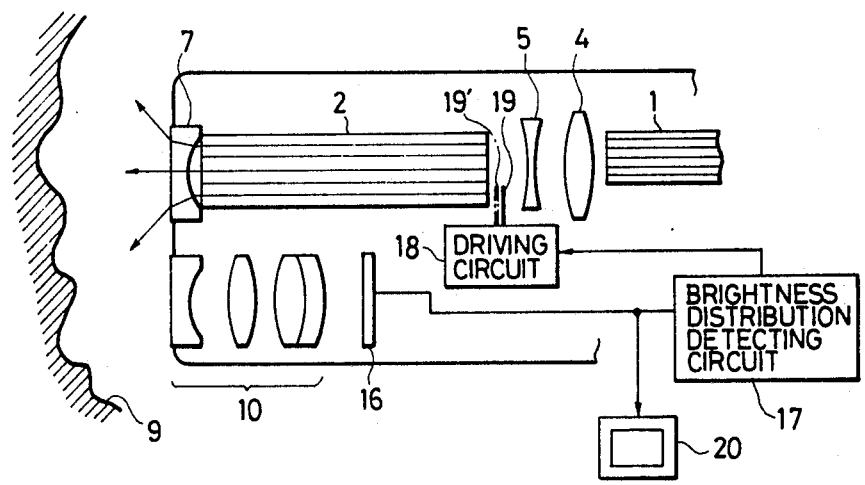

ILLUMINATING OPTICAL SYSTEM FOR ENDOSCOPES

BACKGROUND OF THE INVENTION (a) Field of the Invention

This invention relates to an illuminating optical system for endoscopes wherein a connecting optical system is arranged between a light supplying side light guide and light receiving side light guide.

(b) Description of the Prior Art

In such conventional illuminating optical system for endoscopes of this kind as is mentioned, for example, in Japanese Patent Preliminary Publication No. Sho 55-11216, as shown in FIG. 1, a connecting optical system to be arranged between a light supplying side light guide (light source side light guide) 1 and light receiving side light guide (object side light guide) 2 is formed of a convex lens system 3 and therefore there have been problems that all the peripheral exit light of the exit light out of the exit end face of the light supplying side light guide 1 will be largely bent but all the central exit light will be little bent, therefore, if the light intensity distribution on the exit end face is uneven, the light incident upon the entrance end face of the light receiving side light guide 2 will be uneven in response to the angle, as a result, the exit light of the light receiving side light guide 2 will be also uneven and the light distribution will be uneven within the visual field of the endoscope.

SUMMARY OF THE INVENTION

In view of the above mentioned problems, a primary object of the present invention is to provide an illuminating optical system for endoscopes wherein a uniform light distribution can be obtained.

According to the present invention, this object is attained by forming a connecting optical system to be arranged between a light supplying side light guide and light receiving side light guide of at least one convex lens and at least one concave lens so as to be an afocal system.

According to a preferred formation of the present invention, there are respectively arranged a convex lens to face the exit end of the light supplying side light guide and a concave lens to face the entrance end of the light receiving side light guide.

According to another preferred formation of the present invention, the light receiving side light guide is formed of many fibers arranged to substantially correspond to each other at the entrance end and exit end and at least one light refracting member is arranged in front of the exit end so that a more uniform light distribution may be obtained.

According to a further preferred formation of the present invention, a light intercepting member intercepting a part of the light bundle to uniform the brightness on the surface of an object image is provided between the light supplying side light guide and light receiving side light guide.

This and other objects of the present invention will become more apparent during the course of the following detailed description and appended claims.

BRIEF DESCRIPTION OF THE DRAWINGS

FIG. 9 is a view showing a fifth embodiment of the optical system according to the present invention.

DESCRIPTION OF THE PREFERRED EMBODIMENTS

Figure 2:
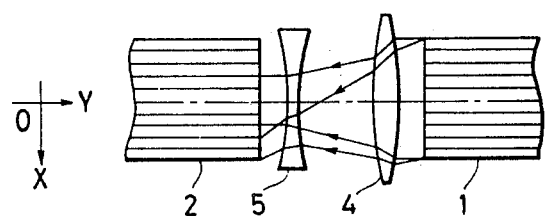
FIG. 2 is a view showing a first embodiment of the connecting optical system in the illuminating optical system for endoscopes according to the present invention.

The present invention shall be explained in detail in the following on the basis of the first embodiment shown in FIG. 2. The reference numerals 4 and 5 represent respectively a convex lens and concave lens arranged between a light supplying side light guide and light receiving side light guide 2 and forming a substantially afocal connecting optical system. That is to say, if the focal distance of the convex lens 4 is represented by $f_1$, the focal distance of the concave lens 5 is represented by $f_2(<0)$ and the distance between both lenses 4 and 5 is represented by d, the relation of $$d = f_1 + f_2 \tag{1}$$

will be substantially established.

Generally, as an afocal system changes only an angular magnification but does not change angles of an incident light and exit light, the peripheral light parallel with the optical axis of the exit light out of the exit end face of the light supplying side light guide will be incident parallelly with the optical axis upon the entrance face of the light receiving side light guide 2, the light oblique to the optical axis will be incident obliquely upon the entrance face, the light parallel with the optical axis of the central exit light will be incident parallelly with the optical axis upon the entrance face and the light oblique to the optical axis will be incident obliquely upon the entrance face. Therefore, even if the light intensity distribution on the exit end face of the light supplying side light guide 1 is uneven, the light incident upon the entrance end face of the light receiving side light guide 2 will not be uneven in response to the angle, as a result, the exit light of the light receiving side light guide will not be uneven and therefore a uniform light distribution will be obtained within the visual field of the endoscope.

By the way, the above mentioned formula (1) need not be always perfectly satisfied.

Figure 3:
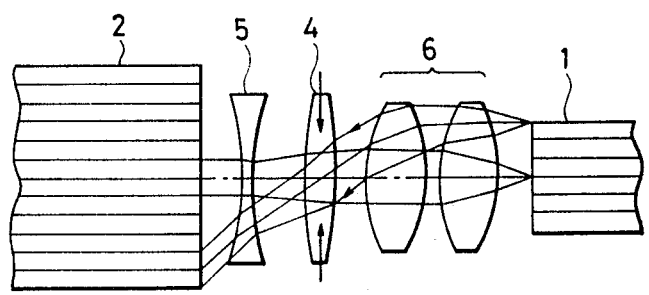
FIG. 3 is a view showing a second embodiment of the connecting optical system according to the present invention.

FIG. 3 shows a second embodiment wherein a convex lens system 6 is arranged in front of the light supplying side light guide 1, a convex lens 4 is placed in the front side focus position of the convex lens system 6 and a concave lens 5 is placed in front of the convex lens 4.

The convex lens 4 and concave lens 5 substantially satisfy the above mentioned formula (1). In this case, there are the same defects as in the above mentioned conventional example but there is an advantage that a light distribution wider than in the above mentioned conventional example is obtained.

Figure 1:
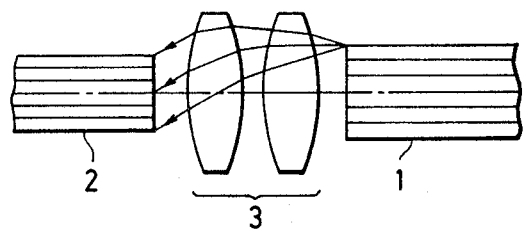
FIG. 1 is a view showing a conventional example of a connecting optical system.
Figure 4:
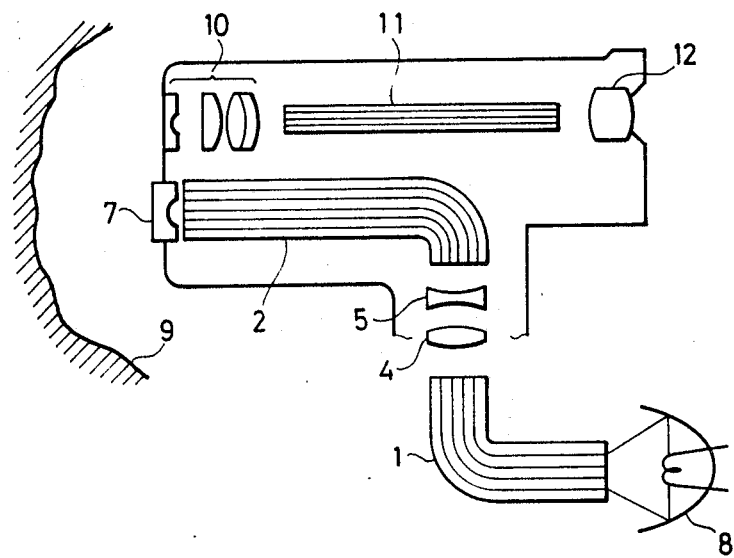
FIG. 4 is a general view of an illuminating optical system for endoscopes using a third embodiment of the connecting optical system according to the present invention.
Figure 5:
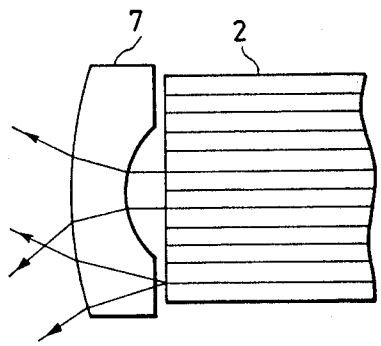
FIG. 5 is a enlarged view of the exit end part of the light receiving side light guide in the third embodiment.

FIG. 4 shows a third embodiment wherein the connecting optical system shown in FIG. 1 is used and a concave lens 7 which is flat in the peripheral part of the surface on the light guide 2 side and is concave in the central part as shown in FIG. 5 is arranged in front (on the object side) of the exit end of the light receiving side light guide 2. By the way, in the light guide 2 to be used, the fibers are arranged to substantially correspond to each other on the entrance side and exit side or the fibers located in the central part of the light guide at the entrance end are so arranged as to be substantially in the central part even at the exit end. The reference numeral 8 represents a light source, 9 represents an object surface, 10 represents an objective lens, 11 represents an image guide and 12 represents an eyepiece.

Figure 6:
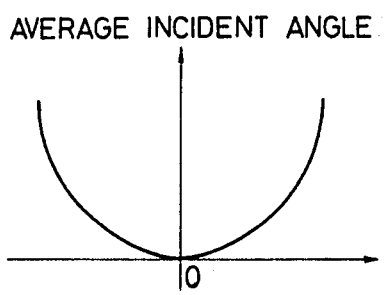
FIG. 6 is a graph showing the average incident angle of the light incident upon the light receiving side light guide in the third embodiment.

In such formation, a more uniform light distribution will be obtained. The reason shall be explained in the following. FIG. 6 is a graph showing the relation between the average incident angle of the light incident upon the light receiving side light guide 2 and the coordinates X of the entrance end face. The incident angle of the light bundle entering the vicinity of the center of the entrance end face is small but the incident angle of the light bundle entering the peripheral side is large.

Figure 7:
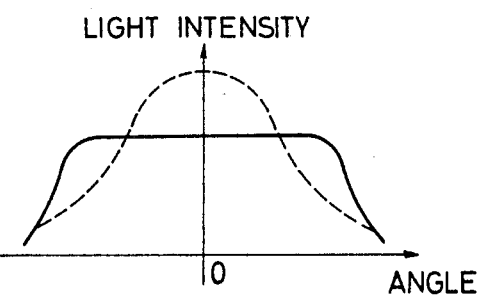
FIG. 7 is a graph showing the light distribution characteristics on the object surface.

Therefore, the light bundle emitting out of the light guide 2 will be small in the exit angle near the center of the exit end face of the light guide but large in the exit angle on the peripheral side and its light distribution characteristics will be as illustrated by the dotted line in FIG. 7. Therefore, if the light bundle near the center is expanded by the action of a concave lens 7, the light distribution characteristics on the object surface 9 will be as illustrated by the solid line in FIG. 7 and a more uniform light distribution will be obtained.

In the embodiment of FIG. 4, for the connecting optical system, the connecting optical system shown in FIG. 3 may be used.

Figure 8:
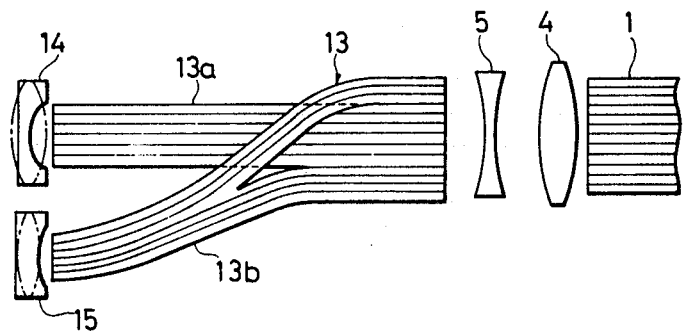
FIG. 8 is a view showing a fourth embodiment of the optical system according to the present invention.

FIG. 8 shows a fourth embodiment wherein a light guide 13 in which fibers in the center of the entrance end and fibers on the peripheral side are forked at the exit end is used for the light receiving side light guide, a concave lens 14 strong in the power is used for the light guide 13a near the center, a concave lens 15 weak in the power is used for the light guide 13b on the peripheral side and both concave lenses 14 and 15 are parallelly placed.

In this embodiment, as shown by the chain lines in FIG. 8, a convex lens strong in the power and a convex lens weak in the power may be used respectively instead of the concave lenses 14 and 15.

FIG. 9 shows a fifth embodiment wherein a solid-state image senser 16 is arranged in the image forming position of the objective lens 10, the brightness distribution of the image surface is detected by a brightness distribution detecting circuit 17, the light bundle illuminating the bright part of the image surface is intercepted by a light intercepting plate 19 inserted between the light supplying side light guide 1 and light receiving side light guide 2 and driven by a driving circuit 18 to uniform the brightness of the image surface. The reference numeral 20 represents a monitor TV. By the way, it will be more effective to place the light intercepting plate 19 between the concave lens 5 and the entrance end surface of the light receiving side light guide 2.

Also, as shown by the chain line in FIG. 9, a liquid crystal plate or electrochromic glass 19' which can be brought to intercept the light by the driving circuit 18 may be used instead of the light intercepting plate 19.

What is claimed is:

1. An illuminating optical system for endoscopes provided with a light supplying side light guide, a light receiving side light guide spaced from and aligned with said light supplying side light guide, and a connecting optical system arranged between said light supplying side light guide and said light receiving side side light guide and causing light emitted from said light supplying side light guide to be incident upon said light receiving side light guide, wherein both said light supplying side light guide and said light receiving side light guide are formed of a plurality of optical fibers, said connecting optical system is an afocal system including a lens having positive refractive power and a lens having negative refractive power arranged in turn from the side of said light supplying side light guide.

2. An illuminating optical system for endoscopes according to claim 1, wherein a lens in which the refractive power on the optical axis is stronger than that on the periphery is arranged in front of the exit end of said light receiving side light guide.

3. An illuminating optical system for endoscopes according to claim 1 further comprising a convex lens system arranged between said conencting optical system and the exit end surface of said light supplying side light guide.

4. An illuminating optical system for endoscopes according to claim 1 wherein said light receiving side light guide has a first exit end formed of fibers located in the central region of the entrance end and a second exit end formed of fibers in the peripheral side region and separated from the first exit end, and said illuminating optical system further comprises a concave lens with a first focal length and arranged in front of said first exit end and a concave lens with a second focal length that is relatively longer than the first focal length and arranged in front of said second exit end.

5. An illuminating optical system for endosopes according to claim 1 wherein said light receiving side light guide has a first exit end formed of fibers located in the centeral region of the entrance end and a second exit end formed of fibers in peripheral side region and separated from the first exit end, and saids illuminating optical system further comprises a concave lens with a first focal length and arranged in front of said first exit end and a concave lens with a second focal length that is relatively longer than the first focal length and arranged in front of said second exit end.

6. An illuminating optical system for endoscopes according to one of claims 1, 2, 4 or 5 further comprising a light intercepting member arranged between said light supplying side light guide and said light receiving side light guide and intercepting a part of the light bundle led to said light receiving side light guide from said light supplying side light guide in response to the brightness distribution on the object image surface.

7. An illuminating optical system for endoscopes according to claim 6, wherein said light intercepting member is arranged between said concave lens and the entrance end of said light receiving side light guide.

8. An illuminating optical system for endoscopes according to claim 6 wherein said light intercepting member is any of a light intercepting plate, liquid crystal plate and electrochromic glass.

* * * * *

UNITED STATES PATENT AND TRADEMARK OFFICE
CERTIFICATE OF CORRECTION

PATENT NO. : 4,721,359

DATED : January 26, 1988

INVENTOR(S) : Kimihiko NISHIOKA; Susumu TAKAHASHI

It is certified that error appears in the above-identified patent and that said Letters Patent is hereby corrected as shown below:

Column 4, line 11, delete "side", second occurrence.

Column 4, line 28, change "conencting" to --connecting--.

Column 4, line 45, change "centeral" to --central--.

Column 4, line 47, change "saids" to --said--.

Signed and Sealed this

Twenty-third Day of August, 1988

*Attest:*

DONALD J. QUIGG

*Attesting Officer*  *Commissioner of Patents and Trademarks*